United States Patent

Schuler

[11] 4,271,837
[45] Jun. 9, 1981

[54] ELECTROSURGICAL APPARATUS

[75] Inventor: Martin Schuler, München, Fed. Rep. of Germany

[73] Assignee: Aesculap-Werke Aktiengesellschaft vormals Jetter & Scheerer, Tuttlingen, Fed. Rep. of Germany

[21] Appl. No.: 3,929

[22] Filed: Jan. 16, 1979

[30] Foreign Application Priority Data

Jan. 17, 1978 [DE] Fed. Rep. of Germany ....... 2801833

[51] Int. Cl.³ ............................................. A61B 17/39
[52] U.S. Cl. ............................ 128/303.14; 128/303.17
[58] Field of Search ........................ 128/303.13, 303.14, 128/303.17

[56] References Cited

U.S. PATENT DOCUMENTS

| 3,923,063 | 12/1975 | Andrews et al. | 128/303.14 |
| 3,964,487 | 6/1976 | Judson | 128/303.14 |
| 4,114,623 | 9/1978 | Meinke et al. | 128/303.14 |
| 4,122,854 | 10/1978 | Blackett | 128/303.13 |
| 4,184,492 | 1/1980 | Meinke et al. | 128/303.14 |
| 4,188,927 | 2/1980 | Harris | 128/303.14 |

FOREIGN PATENT DOCUMENTS

| 1178528 | 9/1974 | Fed. Rep. of Germany | 128/303.14 |
| 2504280 | 11/1976 | Fed. Rep. of Germany | 128/303.14 |
| 855459 | 11/1960 | United Kingdom | 128/303.17 |
| 897961 | 6/1962 | United Kingdom | 128/303.14 |

OTHER PUBLICATIONS

Kowarschik, "Die Diathermie", 1930.
Roth, "Hochspannungstechnik", 1965.
Gerthsen et al., "Physik", 1971.

Primary Examiner—Lee S. Cohen
Attorney, Agent, or Firm—Wigman & Cohen

[57] ABSTRACT

The present invention relates to an electrosurgical cutting device for the cutting and/or coagulation of tissue with RF current. A cutting electrode and a patient plate are connectable to the terminals of a RF generator. A control system, using a condition change arising at the cutting area during cutting as a controlled value, serves to control the RF current produced by the RF generator as a manipulated variable. The invention is characterized in that, for control of the RF-voltage of the RF generator, the control system responds to d-c voltage that arises at the cutting area during cutting with the RF current.

9 Claims, 1 Drawing Figure

U.S. Patent    Jun. 9, 1981    4,271,837
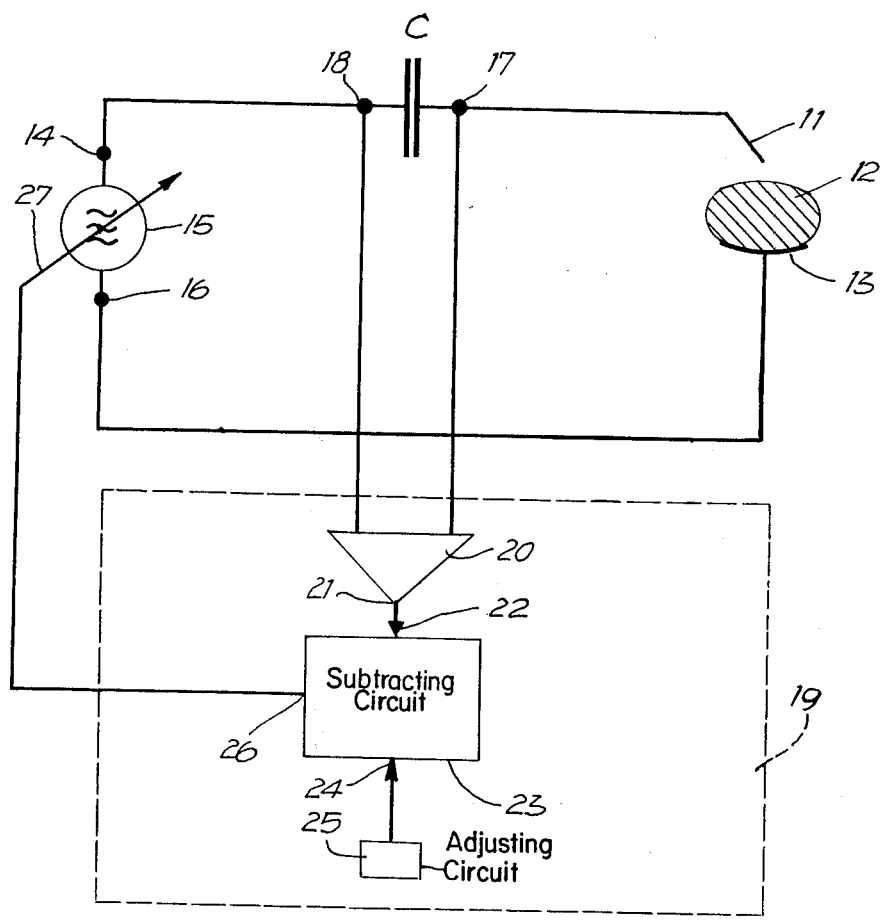

ELECTROSURGICAL APPARATUS

BACKGROUND OF THE INVENTION

1. Field of the Invention

The present invention relates to an electrosurgical cutting device.

2. Description of the Prior Art

A cutting device of this kind is known through West German Pat. No. 2,504,280. The cutting effect of a cutting electrode results mainly because, at the area where the cutting electrode forms a cutting edge and is applied to the tissue, the tissue is heated intensely in the immediate vicinity of the cutting electrode by the RF current which, among other things, forms arcs so that the cells of the tissue burst, thus resulting in a cut in the tissue. Simultaneously, the protein is coagulated by the heating of the tissue so that the capillary vessels severed during the course of cutting are sealed by the coagulation. An advantage lies in that relatively bloodless cuts can be made with the electrosurgical cutting electrode. If the tissue is heated too intensely, however, in addition to the coagulation of the protein, protein disintegration may result, whereby the consequent healing of the cut is impeded.

For the optimal use of an electrosurgical cutting device, it is therefore important that it be possible to keep the temperature of the cutting electrode precisely at an optimal value.

In order to so set the intensity of the RF current through the automatic and sufficiently quick control operation, so that always the intensity of current exists which guarantees the heating of the tissue suitable for the cutting and coagulation process and, on the other hand, prevents the formation of electric arcs in harmful proportions, it is known through the above-cited West German Pat. No. 2,504,280 to transform the luminous effect of the arc produced between the cutting electrode and the tissue by the RF current into the electric signal of an indication device. This transformation is accomplished with the aid of an opto-electrical transformer, e.g., a photoelectrical cell. It is also known through the same prior art patent to analyze the momentary current of the high frequency circuit with an indication device and to obtain from it electrical signals for the point of application, and/or to analyze the momentary intensity of the arc produced by the RF current. Each of these two measures requires a complex circuit. Moreover, it is not guaranteed that the amount of light absorbed by the opto-electrical transformer or the electrical signals obtained through the analysis of the momentary current of the high-frequency circuit correspond to the temperature during cutting, said temperature being the decisive factor here.

SUMMARY OF THE INVENTION

It is the object of the invention to provide an electrosurgical cutting device wherein the temperature of the cutting electrode in the course of cutting can be kept at a desired temperature range with a significantly less complex circuit.

The invention is based on the fact, long known through Dr. Josef Kowarschik's book, "Die Diathermie", Julius Springer, publishers, Vienna and Berlin, 1930, page 216, that low frequency impulses are produced during cutting with RF current. The point in question here is a rectification of the RF current caused at the cutting area. The d-c current impulses, produced by this rectification, must be avoided because they irritate the motor nerves. This must be prevented at all times during an operation. As it is mentioned in the above-named literature, these low-frequency impulses can be prevented by incorporating a capacitor into the electrode circuit.

The inventor has realized, with surprise, that the rectification of the RF voltage produced at the cutting area is a function of the temperature of the cutting electrode and increases with said temperature. The invention is therefore based on the general conception of employing the d-c voltage arising at the cutting area as a gauge for the temperature of the cutting electrode and thus as a gauge for the heating of the tissue during cutting.

Since the d-c voltage formed at the cutting area during RF cutting is a function of the temperature of the cutting electrode, the invention achieves by means of the temperature of the cutting electrode a control of the RF voltage and thus a control of the RF current. The expenditure for circuitry necessary for responding to d-c voltage is extremely small. Moreover, the invention allows the cutting electrode to be always kept at an optimal cutting temperature.

As described above, it is known how to prevent, with a so-called anti-faradisation capacitor, the direct current impulses created at the cutting area by the rectification of the RF current. A preferred embodiment of the invention is therefore accomplished when the d-c voltage measured at the capacitor corresponds essentially to the d-c voltage produced by rectification at the cutting area, or is at least a function of the same. The anti-faradisation capacitor, however, can be also replaced by a d-c voltage source controlled electronically by the d-c voltage produced at the cutting area, said d-c voltage source thus preventing a faradisation current. In this case, the d-c voltage produced directly at the cutting area can be used as a control value.

In a preferred embodiment of the invention, it is possible to adjust the optimal temperature of the cutting electrode. The adjustable circuit is set to a nominal voltage corresponding to the optimal temperature on the cutting electrode.

BRIEF DESCRIPTION OF THE DRAWING

The invention is shown in detail in the single drawing sheet with references to the circuit plan described hereinbelow.

DETAILED DESCRIPTION OF THE DRAWING

The physical structure of an electrosurgical cutting device is adapted to the necessary application and is generally known. In the accompanying circuit plan therefor, a cutting electrode 11, a tissue to be cut 12, and a large patient plate 13, which can be connected to the patient to be operated on, are only schematically indicated.

The cutting electrode 11 is connected to one terminal 17 of a so-called antifaradisation capacitor C, whose other terminal 18 is connected to the output terminal 14 of a RF generator 15, also only schematically shown. The point of reference potential of the RF generator 15 is connected to a second output terminal 16 and this in turn is directly connected to the patient plate 13, so that the circuit of the RF generator 15, carried from the cutting electrode 11 to the patient plate 13 through the tissue 12, is interrupted by the capacitor C for direct current. The capacitor C has a maximum capacity of 5 nanofarads.

When the cutting electrode 11 is placed in contact with the tissue 12, an RF current then flows through the tissue 12, thus causing both the tissue 12 and the cutting electrode 11 touching it to become greatly heated. Electrons are thereby emitted by the cutting electrode 11. This electron emission leads to the RF voltage being rectified at the cutting area, through which a d-c voltage is built up at the capacitor C. A direct current, irritating to the nerves, namely a faradisation current, is prevented because of the capacitor. This d-c voltage is therefore a function of the electron emission of the cutting electrode, which d-c voltage is in its turn a function of the temperature of the cutting electrode. The temperature of the cutting electrode 11 can therefore be ascertained by measuring the d-c voltage at the capacitor C.

In order to utilize this d-c voltage of the capacitor C for control of the generator 15, a control system 19 is provided which comprises a d-c voltage amplifier 20 as an operational amplifier. The terminals 17 and 18 of the capacitor C are connected to the input of this d-c voltage amplifier 20, so that the d-c voltage arising at the capacitor C is only negligibly influenced by this connection, as a result of the high input resistance of the d-c voltage amplifier 20 which is designed as an "operational" type of amplifier. The output 21 of the d-c voltage amplifier 20 is connected to the input 22 of a subtracting circuit 23, which is also designed as an operational amplifier, so that the d-c voltage prevailing at the output of the d-c voltage amplifier 20 as an actual voltage is also only negligibly influenced by this connection, due to the low output resistance of the d-c voltage amplifier 20 and due to the high input resistance of the subtracting circuit 23. This amplified direct current voltage is used as an actual voltage in the control system 19. A second input 24 of the subtracting circuit 23 is connected to an adjustable circuit 25 for producing a nominal voltage, e.g., with the tapping of a potentiometer switched into a d-c circuit (not shown). At the output 26 of the subtracting circuit 23 there prevails the differential voltage:

$$U_{diff} = U_{nom.} - U_{act.}$$

$U_{nom.}$ means the adjusted nominal voltage and $U_{act.}$ means the actual voltage. Said output 26 is connected to a control input 27 of the generator 15.

The RF generator 15 is so designed in the known way that, with a d-c voltage of zero at the control input 27, it causes a middle RF voltage necessary for the operation. This middle voltage increases with a positive differential voltage $U_{diff}$ when it is present and drops with a negative differential $U_{diff}$ with the absolute value of this voltage. Through changes in the nominal voltage $U_{nom.}$ by means of the controllable circuit 25, the automatically self-regulating RF voltage of the generator 15 can therefore be set within certain limits close to a particular value at which the desired optimal temperature at the cutting electrode prevails.

The d-c voltage amplifier 20, the subtracting circuit 23, and the controllable circuit 25 therefore form the control system 19, which controls the RF voltage produced by the RF generator 15 as a manipulated variable, with the d-c voltage at the capacitor C as a controlled value.

I claim:

1. Electrosurgical apparatus for operating on an operating area of a tissue of a patient with high frequency electrical energy so that a d-c voltage is produced by rectification of the high frequency electrical energy in the operating area which rectified voltage is used to maintain an optimal temperature therein, comprising:
    surgical electrode means for operating on the operating area,
    first connecting means for connecting the patient to a point of reference potential,
    means for generating high frequency voltage between said electrode means and said point of reference potential, and
    control means, responsive to said d-c voltage produced in the operating area and to a predetermined nominal d-c voltage for varying the high frequency voltage generated by said generating means to maintain said surgical electrode means at a desired temperature.

2. Electrosurgical apparatus according to claim 1, wherein said control means comprises first circuit means for amplifying said d-c voltage.

3. Electrosurgical apparatus according to claim 2, further comprising:
    second connecting means for connecting said generating means to said surgical electrode means, said second connecting means comprising a capacitor means for storing said d-c voltage, and
    third connecting means for tapping off said d-c voltage from said capacitor means and for guiding said d-c voltage to said first circuit means.

4. Electrosurgical apparatus according to claim 3, wherein said control means further comprises adjustable second circuit means for producing said predetermined nominal voltage and third circuit means for forming a voltage differential between said nominal voltage and said amplified d-c voltage, said third circuit means having a first input for said amplified d-c voltage, a second input for said nominal voltage and an output for said voltage differential.

5. Electrosurgical apparatus according to claim 4, further comprising:
    fourth connecting means for connecting said output to said generating means for controlling said high frequency voltage.

6. Electrosurgical apparatus according to claim 4, wherein at least one of said first and said third circuit means is a subtracting amplifier.

7. Electrosurgical apparatus according to claim 1, wherein said surgical electrode means is a cutting electrode for cutting the tissue with the high frequency electrical energy and wherein said first connecting means comprises a patient plate for applying said reference potential to the body of the patient.

8. Electrosurgical apparatus according to claim 1, wherein said d-c voltage produced in the operating area is proportional to the temperature at said area of tissue.

9. Electrosurgical apparatus for operating on an operating area of tissue of a patient with high frequency electrical energy so that a d-c voltage, proportional to the temperature at said area of tissue, is produced by rectification of the high frequency electrical energy in the operating area which rectified voltage is used to maintain an optimal temperature therein, comprising:
    surgical electrode means for operating on the operating area,
    first connecting means for connecting the patient to a point of reference potential, means for generating high frequency voltage between said electrode means and said point of reference potential, and control means, responsive to said temperature proportional d-c voltage produced in the operating area and to a predetermined nominal d-c voltage, for varying the high frequency voltage generated by said generating means to maintain said surgical electrode means at a desired temperature.

* * * * *